United States Patent
Nishii et al.

(10) Patent No.: US 7,841,772 B2
(45) Date of Patent: Nov. 30, 2010

(54) IMAGING APPARATUS

(75) Inventors: Yuichi Nishii, Tokyo (JP); Masahiro Abe, Yamato (JP); Hideto Shiozawa, Suwa (JP); Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 16 days.

(21) Appl. No.: 12/270,379

(22) Filed: Nov. 13, 2008

(65) Prior Publication Data
US 2009/0136000 A1    May 28, 2009

(30) Foreign Application Priority Data
Nov. 28, 2007   (JP)   ............... 2007-307891

(51) Int. Cl.
*A61B 6/08*    (2006.01)
(52) U.S. Cl. ........................... 378/206; 378/63
(58) Field of Classification Search ............ 378/63, 378/206, 98.3
See application file for complete search history.

(56) References Cited

U.S. PATENT DOCUMENTS 6,473,489 B2 * 10/2002 Bani-Hashemi et al. ....... 378/63
6,783,275 B2 * 8/2004 Ghelmansarai ............ 378/206

FOREIGN PATENT DOCUMENTS

JP    54-158984    12/1979

* cited by examiner

*Primary Examiner*—Jurie Yun
(74) *Attorney, Agent, or Firm*—Cowan, Liebowitz & Latman, P.C.

(57) ABSTRACT

An imaging apparatus in which positions of an X-ray image and optical image of a subject can be brought into registration with each other is provided. A half-mirror is provided between the X-ray source and subject and is configured to pass X-rays and reflect visible light. A TV camera captures the optical image of the surface of the subject reflected by the half-mirror. A display unit displays the optical image captured by the TV camera together with a reference mark indicating the reference position of this optical image, and displays, in superimposed form, an X-ray image obtained by capturing a prescribed reference object as a subject by using an X-ray imaging unit. An adjusting unit adjusts position and attitude of an X-ray detector in such a manner that the reference object displayed by the display unit will coincide with the reference mark.

6 Claims, 8 Drawing Sheets

IMAGING APPARATUS

BACKGROUND OF THE INVENTION

1. Field of the Invention

The present invention relates to an imaging apparatus for capturing a fluoroscopic image of a subject.

2. Description of the Related Art

Flat-panel detectors that output digital data are now widely used instead of conventional screen/film systems in recent X-ray imaging systems. A flat-panel detector is so adapted that electric charge (referred to as "signal charge" below) proportional to X-ray dosage accumulates in each of a number of two-dimensionally arrayed detecting elements, and the accumulated signal charges are read out to a signal output line sequentially via TFTs (thin-film transistors) having a switching function. Signal charge that has been output to the signal output line is subjected to a charge-to-voltage conversion and is displayed upon being converted to a digital signal by an A/D converter.

An X-ray imaging apparatus can be classified broadly into three types, namely an upright type in which the subject is imaged in an upright attitude, an inclined type in which the subject is imaged while lying upon a bed, and a portable (cassette) type that can be moved about and can image a subject in any attitude.

In order to provide a guide for making an incision or to recognize the irradiation field when surgery is performed, it has been proposed to use an optical camera to capture the optical image of the subject surface in the imaging plane of the X-ray imaging apparatus, and to display the image obtained. Japanese Patent Laid-Open No. 54-158984 discloses a technique in which an optical image of the surface of a subject is captured by an optical camera via a half-mirror placed between an X-ray source and the subject so as to obtain an optical image having the same direction as the imaging direction of the X-ray imaging apparatus, with the captured image being displayed on a monitor.

The arrangement disclosed in Japanese Patent Laid-Open No. 54-158984 is premised on the fact that there will always be a stable relative positional relationship among the X-ray source, an X-ray detector that detects X-rays and an optical imaging unit for capturing the optical image of the subject surface. However, there is the possibility that this relative positional relationship will be disturbed, particularly in the case of a portable X-ray imaging apparatus.

SUMMARY OF THE INVENTION

Accordingly, the present invention seeks to provide an imaging apparatus in which the relative positional relationship between an X-ray detector and an optical imaging unit can be corrected, thereby bringing the positions of an X-ray image and optical image of a subject into registration.

According to one aspect of the present invention, an imaging apparatus in which positions of an X-ray image and optical image of a subject can be brought into registration with each other is provided. A half-mirror is provided between the X-ray source and subject and is configured to pass X-rays and reflect visible light. A TV camera captures the optical image of the surface of the subject reflected by the half-mirror. A display unit displays the optical image captured by the TV camera together with a reference mark indicating the reference position of this optical image, and displays, in superimposed form, an X-ray image obtained by capturing a prescribed reference object as a subject by using an X-ray imaging unit. An adjusting unit adjusts position and attitude of an X-ray detector in such a manner that the reference object displayed by the display unit will coincide with the reference mark.

Further features of the present invention will become apparent from the following description of exemplary embodiments with reference to the attached drawings.

DESCRIPTION OF THE EMBODIMENTS

Various exemplary embodiments, features and aspects of the present invention will be described in detail below with reference to the drawings.

Figure 1:
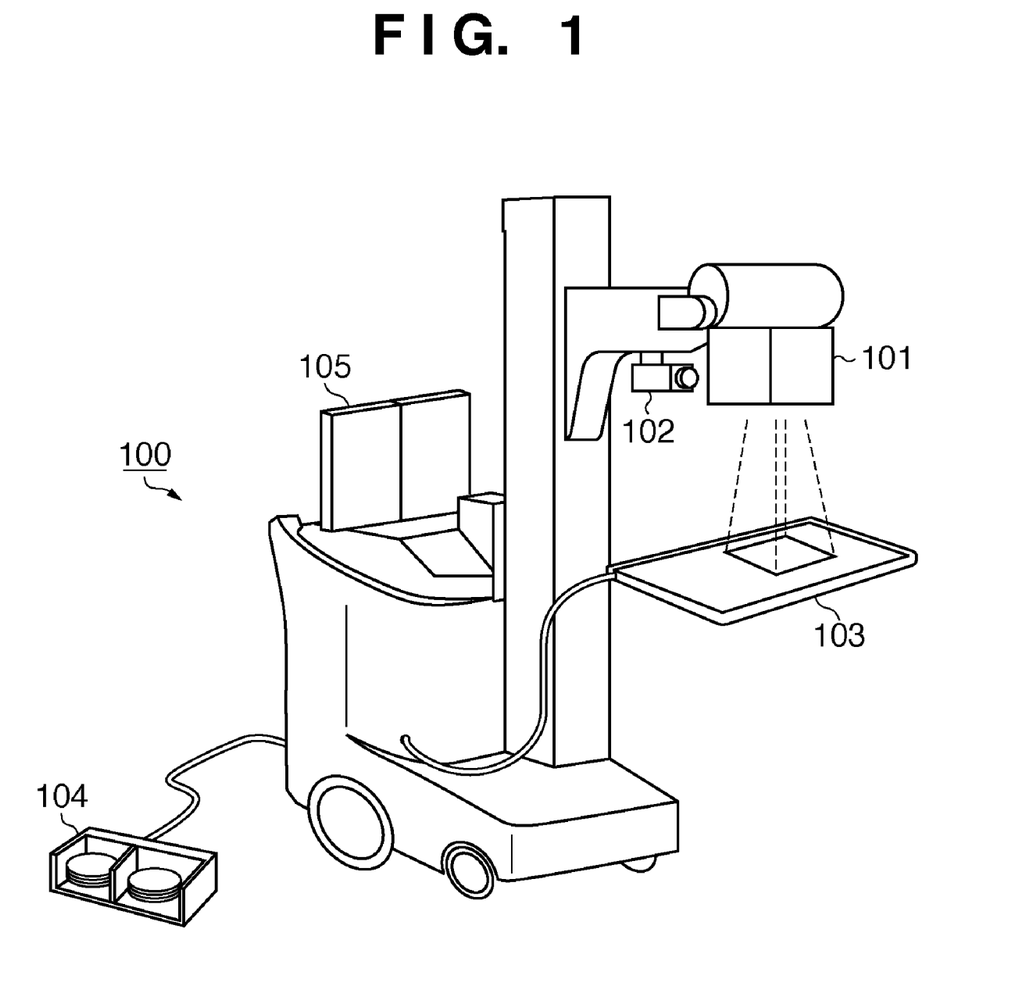
FIG. 1 is a perspective view illustrating the external appearance of an X-ray diagnosis cart according to an embodiment of the present invention.

FIG. 1 is a perspective view illustrating the external appearance of an X-ray diagnosis cart 100 according to an embodiment of the present invention.

The X-ray diagnosis cart 100 is a portable X-ray imaging apparatus that includes an X-ray generator 101, a TV camera 102, an X-ray detector 103, a foot pedal 104 and a display unit 105.

The X-ray generator 101 has a mechanism for generating X-rays that irradiate a subject. Specifically, the X-ray generator 101 includes an X-ray tube serving as an X-ray source, and an X-ray aperture for delimiting the zone of X-ray irradiation.

The TV camera 102 serving as an optical imaging unit is placed at a position conjugate with respect to the X-ray tube via a half-mirror provided inside the X-ray generator 101 and is capable of capturing the optical image of the surface of a subject in an X-ray irradiation zone. Further, the TV camera 102 in this embodiment has a well-known zoom adjustment mechanism. The positional relationship between the TV camera 102 and the X-ray generator 101 will be described later.

An X-ray imaging unit for capturing the X-ray image of the subject is constructed by the X-ray generator 101 and X-ray detector 103. The subject is placed upon the X-ray detector 103 and is irradiated by the X-ray generator 101. The X-ray detector 103 detects X-rays that pass through the subject, thereby acquiring an image signal representing a fluoroscopic image of the subject.

The foot pedal 104 is an input unit for instructing the apparatus to turn X-ray irradiation on and off. The display unit 105, which is constituted by a CRT or liquid crystal display, presents a GUI (Graphical User Interface) for operating the apparatus and displays the X-ray image of the subject and the optical image captured by the TV camera 102. In accordance with the command from the foot pedal 104, the display unit 105 is capable of switching between display of the X-ray image and optical image of the subject and is also capable of displaying these in superimposed form. Further, the display unit 105 displays a reference mark, which indicates the reference position of the optical image, together with the optical image captured by the TV camera 102. By way of example, the reference mark may be one formed on a screen placed on the display surface of the display unit 105 or one obtained by displaying image data representing a reference mark.

It should be noted that the X-ray diagnosis cart 100 also includes other input units, such as a keyboard and mouse. It goes without saying that a control unit for controlling the X-ray imaging apparatus is incorporated within the housing of the X-ray diagnosis cart 100.

Figure 2:
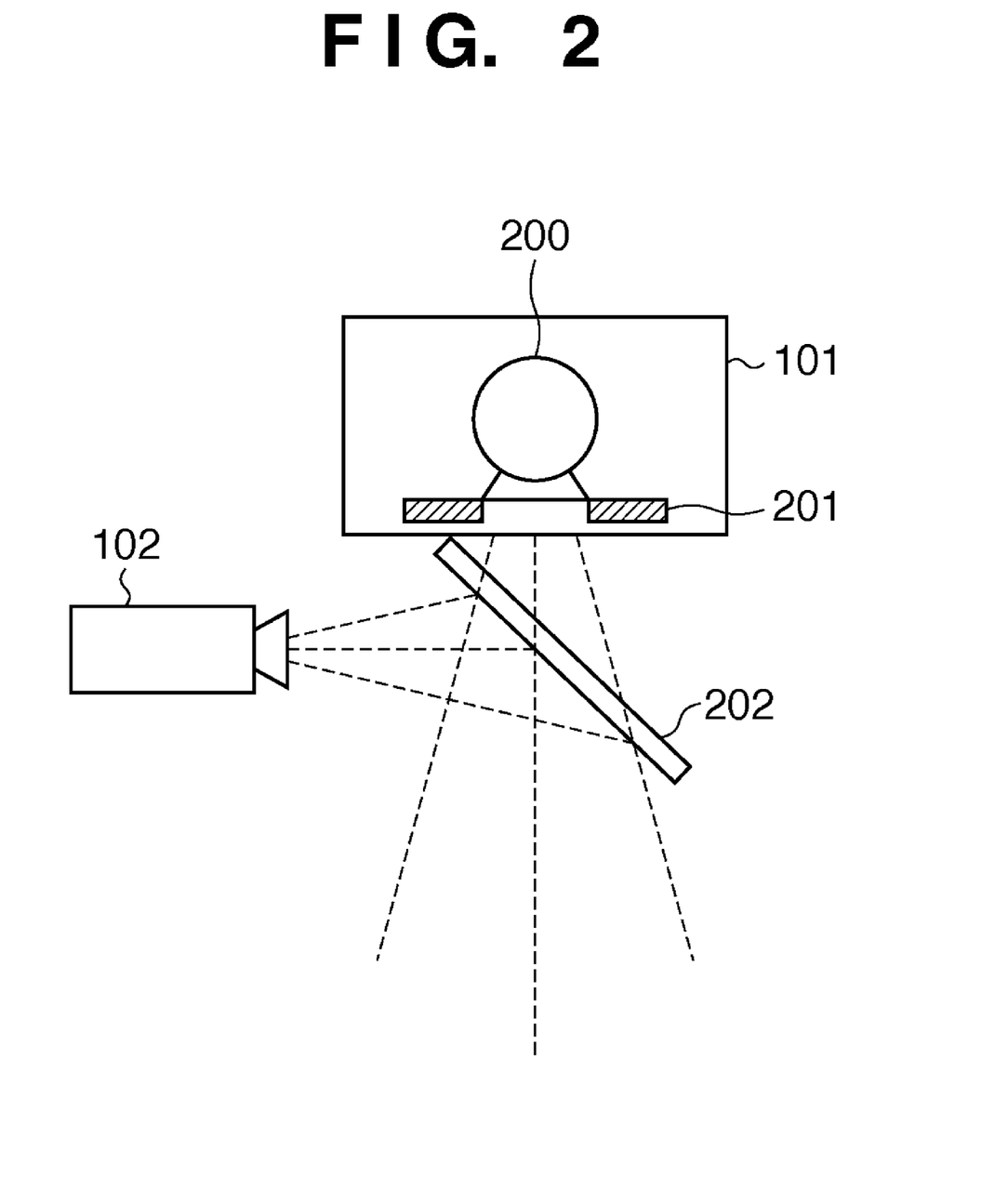
FIG. 2 is a diagram illustrating the configuration of an X-ray generator and TV camera in this embodiment.

Next, the details of the configuration of X-ray generator 101 will be described with reference to FIG. 2, which is a diagram illustrating the positional relationship and configuration of the X-ray generator 101 and TV camera 102.

The X-ray generator 101 has an X-ray tube 200 serving as the X-ray source, and a collimator 201 for limiting the irradiation direction and irradiation area of X-ray emitted from the X-ray tube 200. The X-ray generator 101 further includes a half-mirror 202 provided at a position between the collimator 201 and subject for passing X-rays and reflecting visible light. While the X-rays from the X-ray generator 101 pass through the half-mirror 202 and irradiate the subject, the optical image of the subject surface is reflected by the half-mirror 202 and input to the TV camera 102. As a result, the TV camera 102 is capable of capturing the optical image of the subject surface in a direction the same as the irradiation direction of the X-rays.

Figure 10:
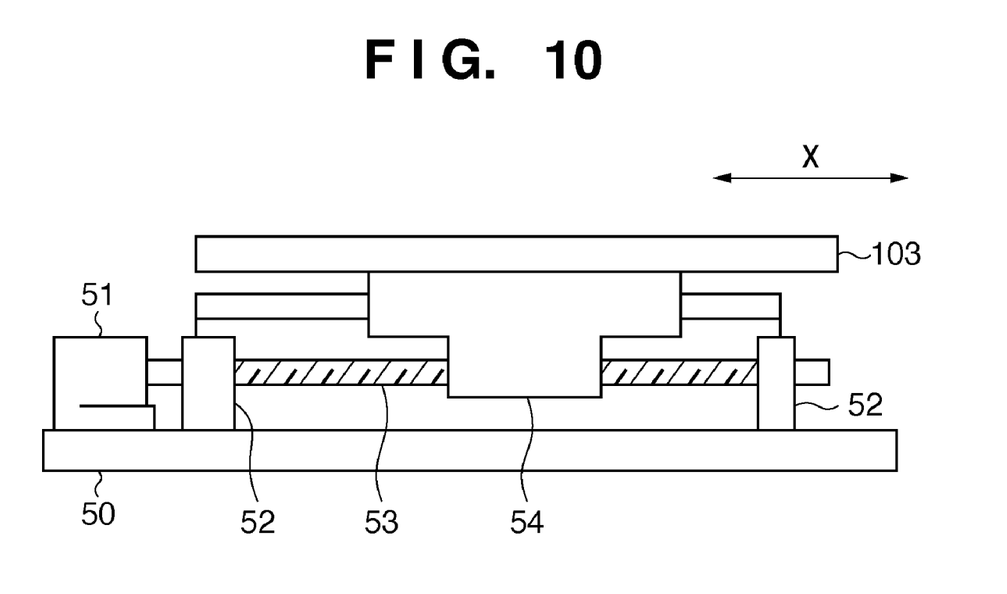
FIG. 10 is a diagram illustrating an example of a mechanism for moving an X-ray detector.
Figure 11:
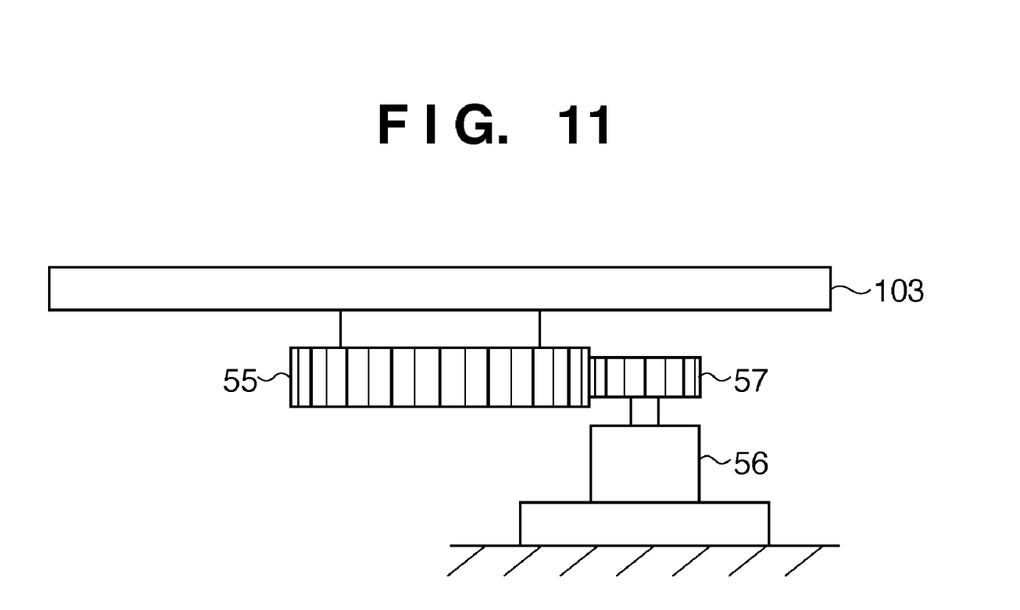
FIG. 11 is a diagram illustrating an example of a mechanism for rotating an X-ray detector.

The X-ray detector 103 is so adapted that the position and attitude thereof can be adjusted. For example, the X-ray detector 103 is capable of being moved in one direction (the X direction) of the horizontal directions by a well-known feed screw mechanism of the kind depicted in FIG. 10. Specifically, a driving motor 51 and feed screw supports 52, 52 are secured to a base 50. When the driving motor 51 rotates, a coaxially coupled feed screw 53 rotates so that the position of the X-ray detector 103 along the X direction can be adjusted via a feed screw nut 54. Further, although not illustrated, it is so arranged that movement in the Y direction perpendicular to the X direction can be performed by a similar mechanism. As illustrated in FIG. 11, a driven gear 55 is secured underneath the X-ray detector 103 at the center thereof, and a driving gear 57 fixed to the output shaft of a driving motor 56 is in mesh with the driven gear 55. In accordance with this arrangement, the angle of rotation of the X-ray detector 103 in the horizontal direction can be adjusted by driving the driving motor 56.

Figure 3:
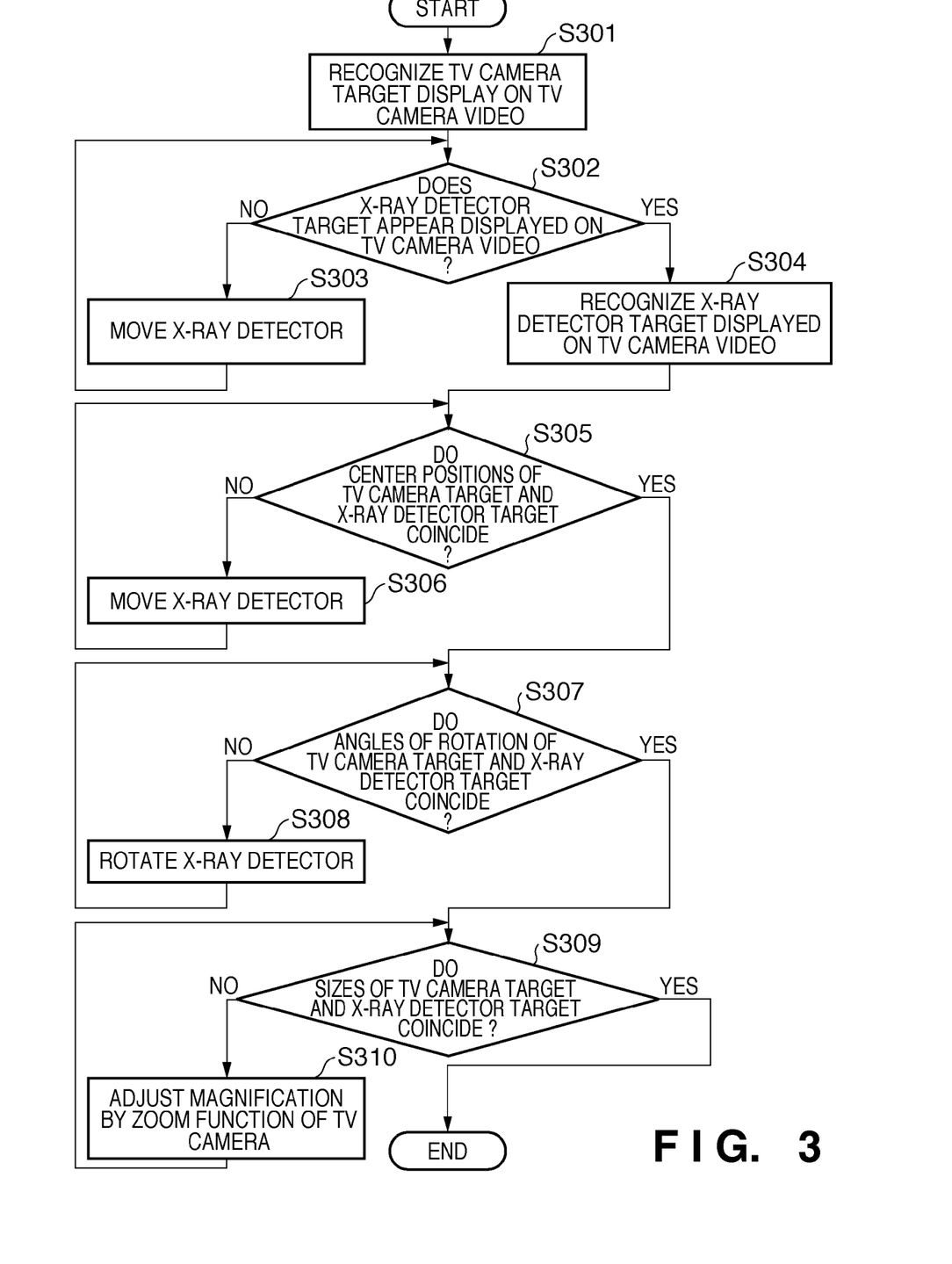
FIG. 3 is a flowchart illustrating an example of processing for achieving relative alignment between a TV camera and X-ray detector in this embodiment.

An example of processing for achieving relative alignment between the TV camera 102 and X-ray detector 103 of this embodiment will now be described with reference to the flowchart of FIG. 3.

First, a prescribed reference object is placed on the X-ray detector 103 as a subject, the reference object is irradiated with X-rays from the X-ray generator 101 and the X-ray image thereof is acquired. By way of example, a phantom having a shape the same as that of the above-mentioned reference mark and that contains a certain amount of calcium is used as the reference object. In this processing, the X-ray image of the reference object is used as the target of the X-ray detector.

The display unit 105 displays the optical image, which has been captured by the TV camera 102, together with the reference mark. In this processing, the reference mark is used as the target of the TV camera. The display unit 105 displays, in superimposed form, the X-ray detector target, which is the X-ray image of the reference object obtained by the X-ray detector 103.

Figure 4:
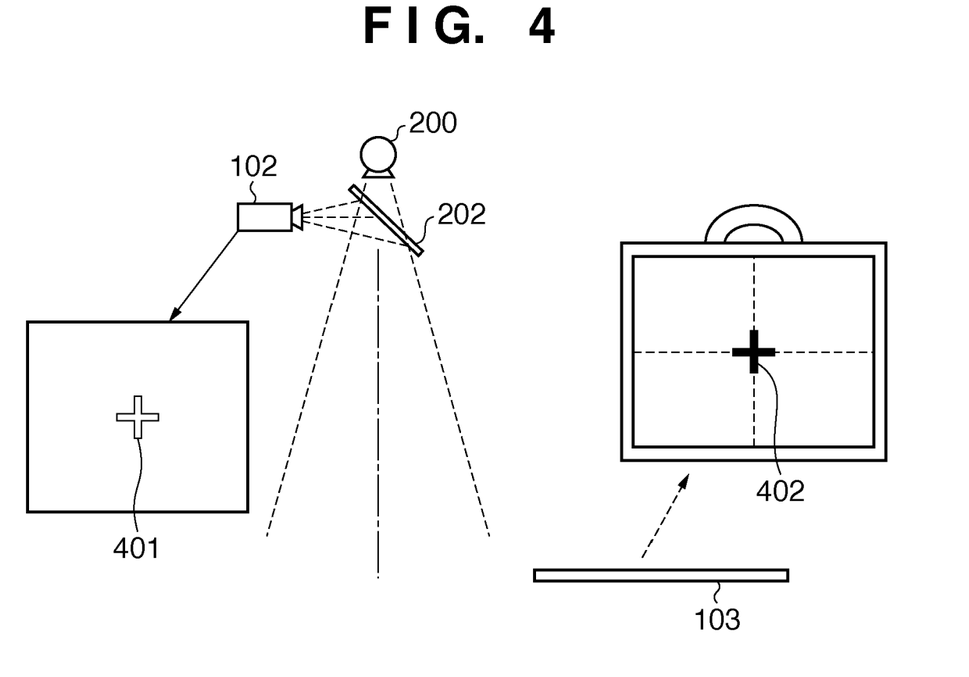
FIGS. 4 to 8 are diagrams useful in describing processing for achieving relative alignment between a TV camera and X-ray detector in this embodiment.

The operator recognizes a TV camera target 401 (FIGS. 4 to 8) displayed on the display unit 105 (S301). Next, the operator checks to determine whether an X-ray detector target 402 (FIGS. 4 to 8) is appearing on the video of the display unit 105 (S302). If the X-ray detector target 402 does not appear in the state shown in FIG. 4, then the X-ray detector 103 is moved until the X-ray detector target 402 comes into view, as illustrated in FIG. 5.

Figure 5:
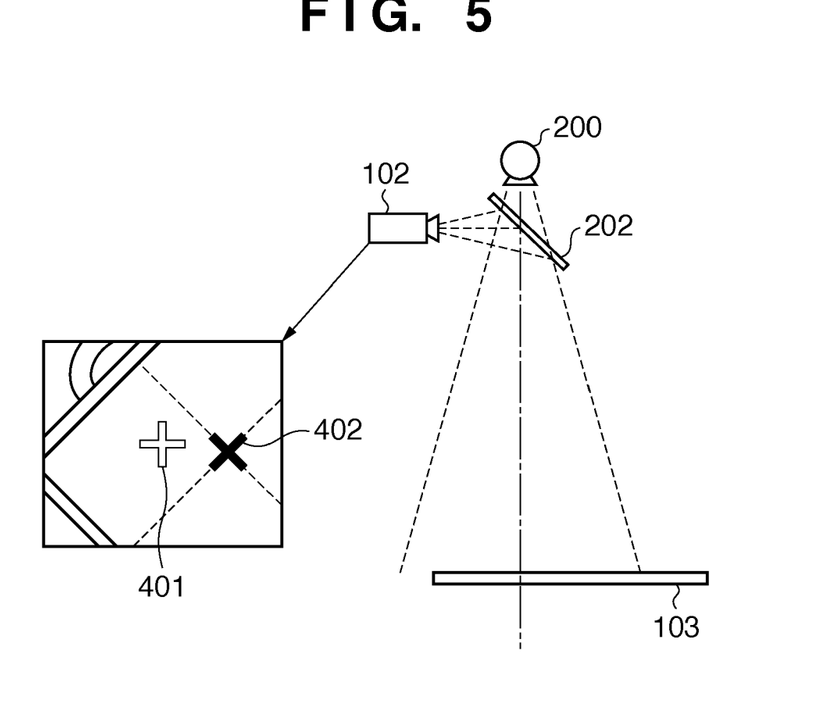
Figure 6:
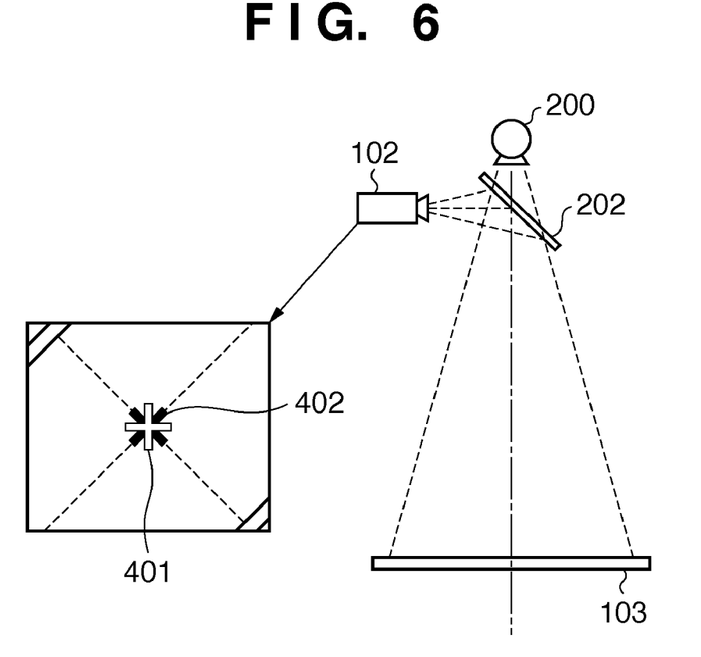

If it is recognized that the X-ray detector target 402 has come into view as shown in FIG. 5 (S304), then the operator checks to determine whether the center position of the TV camera target 401 and the center position of the X-ray detector target 402 coincide (S305). If the two center positions do not coincide, the X-ray detector 103 is moved until the two center positions come into coincidence, as illustrated in FIG. 6 (S306).

Figure 7:
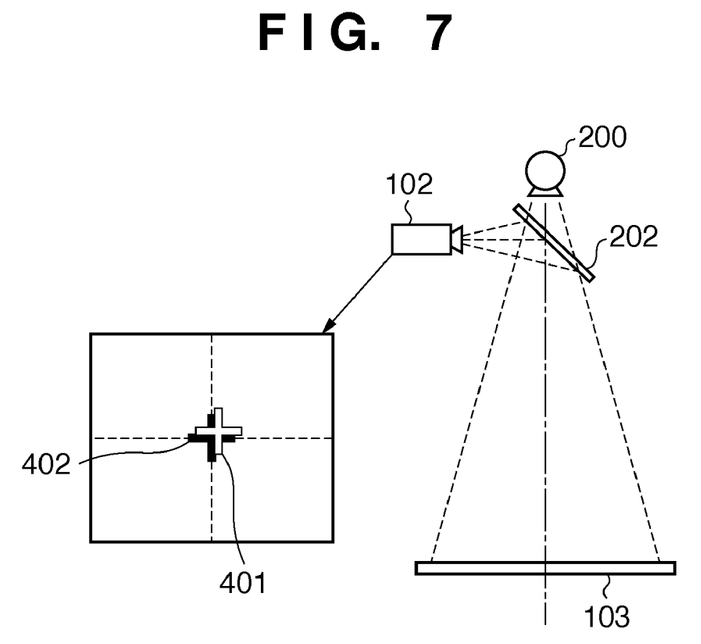

If it has been confirmed that the center position of the TV camera target 401 and the center position of the X-ray detector target 402 coincide, then the operator checks to determine whether the angle of rotation of the TV camera target 401 and the angle of rotation of the X-ray detector target 402 coincide (S307). If the two angles of rotation do not coincide, the X-ray detector 103 is rotated until the two come into coincidence, as illustrated in FIG. 7 (S308).

Figure 8:
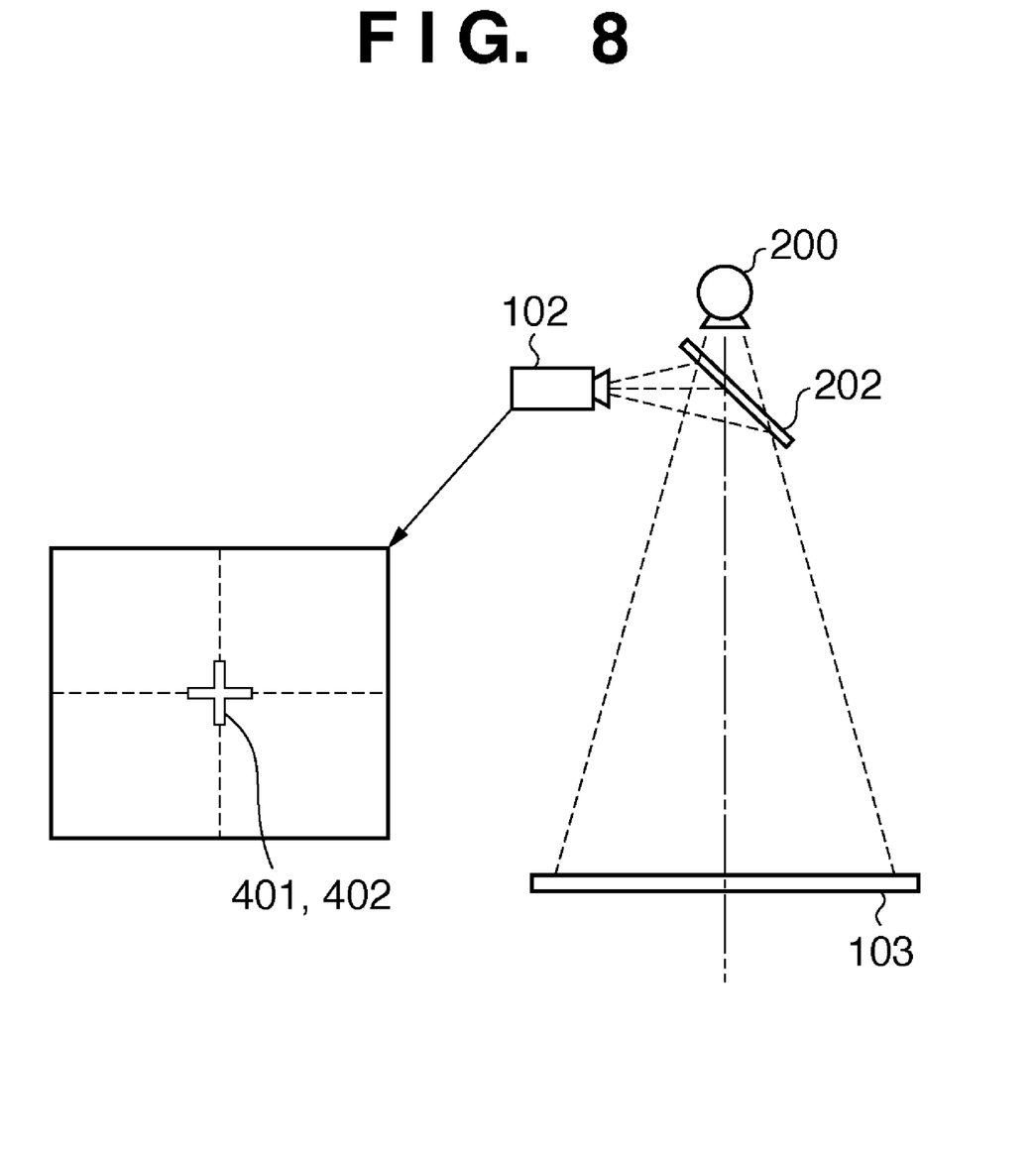

If it has been confirmed that the angle of rotation of the TV camera target 401 and the angle of rotation of the X-ray detector target 402 coincide, then, in this embodiment, the operator further determines whether size of the TV camera target 401 and the size of the X-ray detector target 402 agree (S309). If the two do not agree, then the zoom magnification is adjusted by the zoom function of the TV camera 102 until the two sizes come into agreement, as illustrated in FIG. 8 (S310).

It should be noted that it is permissible to change the order of adjustment of the center positions at S305 and S306, the correction of the angle of rotation at S307 and S308, and the adjustment of zoom magnification at S309 and S310.

Further, with regard to S306 at which the X-ray detector 103 is moved in order to correct the center position of the X-ray detector target 402, it is possible to replace this with image processing of the image acquired by the TV camera 102 or with image processing of the X-ray image of the X-ray image acquired by the X-ray detector 103. Further, it is possible to correct the center position of the X-ray detector target 402 by moving the X-ray generator 101 and the TV camera 102.

Further, with regard to S308 at which the X-ray detector 103 is rotated in order to correct the angle of rotation of the X-ray detector target 402, it is possible to replace this with image processing of the image acquired by the TV camera 102. Alternatively, it is possible substitute rotation of the TV camera 102 or rotation of the optical system of the TV camera 102. Further, it is possible to correct the angle of rotation of the X-ray detector target 402 by moving the X-ray generator 101 and the TV camera 102.

Further, with regard to S310 at which magnification is adjusted by the zoom function of the TV camera 102, it is possible to replace this with image processing of the image acquired by the TV camera 102 or with movement of the TV camera 102. Alternatively it is possible to substitute image processing of the image acquired by the X-ray detector 103, movement of the X-ray tube 200 and selection of X-ray focal point.

Figure 9A:
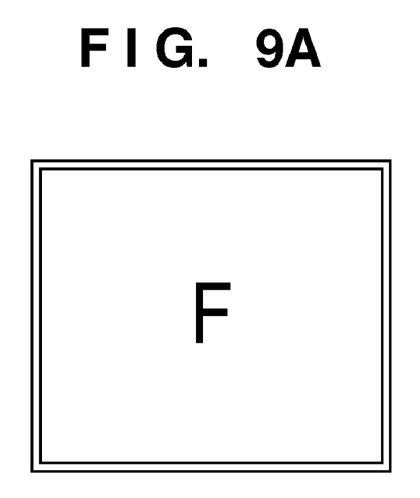
FIGS. 9A to 9C are diagrams illustrating examples of a plurality of targets arranged so as not to have line symmetry and point symmetry.
Figure 9B:
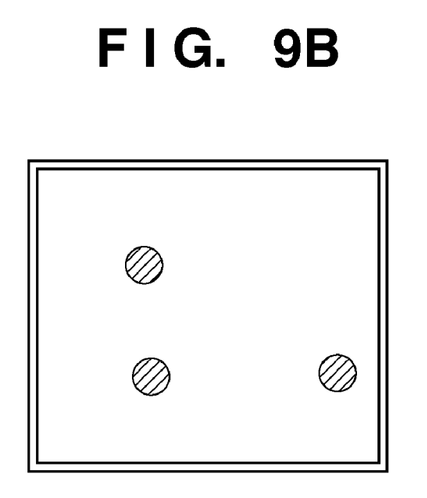

Further, in the example illustrated in FIGS. 4 to 8, a cross-hair target is used as the TV camera target 401 and X-ray detector target 402. However, in the case of a cross-hair target, there is the possibility that the coincidence of the targets will be achieved in a state in which they have been flipped vertically and/or horizontally. Accordingly, in order to perform a more robust correction in which such vertical or horizontal flipping will not occur, it will suffice to use a shape that does not have line symmetry and point symmetry, as illustrated in FIG. 9A. Alternatively, use may be made of a plurality of marks and objects arranged so as not to have line symmetry and point symmetry, as illustrated in FIG. 9B.

Figure 9C:
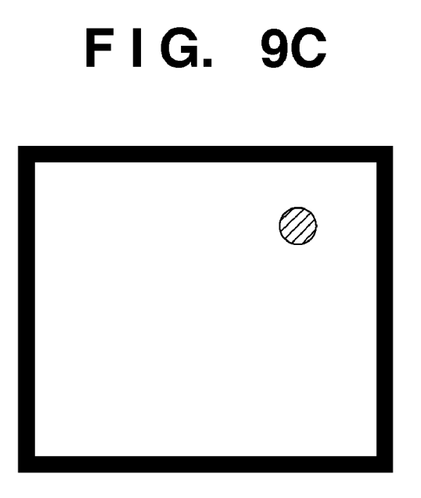

Further, if a mark corresponding to the imaging frame of the TV camera 102 and an object placed on an outer frame of the X-ray detector 103 are used as targets, as illustrated in FIG. 9C, it is possible to create targets that do not possess line symmetry and point symmetry merely by adding on an object having a simple shape.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-307891, filed Nov. 28, 2007, which is hereby incorporated by reference herein in its entirety.

What is claimed is:

1. An imaging apparatus comprising:
    an X-ray imaging unit configured to capture an X-ray image of a subject by detecting X-rays, which have been generated by an X-ray source and have passed through the subject, using an X-ray detector;
    a half-mirror provided between the X-ray source and subject and configured to pass X-rays and reflect visible light;
    an optical imaging unit configured to capture an optical image of the surface of the subject, wherein the optical image has been reflected by said half-mirror;
    a display unit configured to display a point asymmetric reference mark, which indicates a reference position of the optical image, together with the optical image captured by said optical imaging unit, and to display, in superimposed form, an X-ray image obtained by imaging a prescribed reference object having a shape the same as that of the point asymmetric reference mark as a subject using said X-ray imaging unit; and
    an adjusting unit configured to adjust the position and angle of rotation of at least one of either said X-ray imaging unit or said optical imaging unit in such a manner that the reference object displayed by said display unit will coincide with the point asymmetric reference mark.

2. The apparatus according to claim 1, wherein said adjusting unit further includes a magnification adjusting unit configured to adjust zoom magnification of said optical imaging unit in such a manner that sizes of the reference object and reference mark displayed by said display unit will be the same.

3. The apparatus according to claim 1, wherein the reference mark and reference object are cross-hair shaped.

4. The apparatus according to claim 1, wherein a plurality of marks constituting the reference mark include a mark corresponding to an image frame of said optical imaging unit, and a plurality of objects constituting the reference object include an object placed on an outer frame of said X-ray detector.

5. In an imaging apparatus having
    an X-ray imaging unit configured to capture an X-ray image of a subject by detecting X-rays, which have been generated by an X-ray source and have passed through the subject, using an X-ray detector,
    a half-mirror provided between the X-ray source and subject and configured to pass X-rays and reflect visible light,
    an optical imaging unit configured to capture an optical image of the surface of the subject based upon the visible light reflected by the half-mirror,
    a display unit configured to display a point asymmetric reference mark, which indicates a reference position of the optical image, together with the optical image captured by the optical imaging unit, and to display, in superimposed form, an X-ray image captured by the X-ray imaging unit, and
    an adjusting unit configured to adjust the position and angle of rotation of the X-ray detector, a method of bringing the X-ray imaging unit and the X-ray detector into relative alignment, the method comprising the steps of:
    imaging a prescribed reference object having a shape the same as that of the point asymmetric reference mark as a subject using the X-ray imaging unit;
    moving the X-ray detector by the adjusting unit in such a manner that center position of the reference object displayed by the display unit will coincide with center position of the point asymmetric reference mark; and
    rotating the X-ray detector by the adjusting unit in such a manner that angle of rotation of the reference object displayed by the display unit will coincide with angle of rotation of the point asymmetric reference mark.

6. The method according to claim 5, wherein the optical imaging unit has a zoom adjusting unit configured to adjust zoom magnification, and said method further comprises a step of adjusting zoom magnification of the X-ray imaging unit in such a manner that sizes of the reference object and reference mark displayed by the display unit will be the same.

* * * * *